US011633235B2

(12) United States Patent
Shekhar et al.

(10) Patent No.: US 11,633,235 B2
(45) Date of Patent: Apr. 25, 2023

(54) HYBRID HARDWARE AND COMPUTER VISION-BASED TRACKING SYSTEM AND METHOD

(71) Applicants: CHILDREN'S NATIONAL MEDICAL CENTER, Washington, DC (US); IGI TECHNOLOGIES, College Park, MD (US)

(72) Inventors: Raj Shekhar, Washington, DC (US); William Plishker, College Park, MD (US); Xinyang Liu, Washington, DC (US)

(73) Assignees: CHILDREN'S NATIONAL MEDICAL CENTER, Washington, DC (US); IGI TECHNOLOGIES, College Park, MD (US)

( * ) Notice: Subject to any disclaimer, the term of this patent is extended or adjusted under 35 U.S.C. 154(b) by 353 days.

(21) Appl. No.: 16/634,713

(22) PCT Filed: Jul. 31, 2018

(86) PCT No.: PCT/US2018/044604
§ 371 (c)(1),
(2) Date: Jan. 28, 2020

(87) PCT Pub. No.: WO2019/028021
PCT Pub. Date: Feb. 7, 2019

(65) Prior Publication Data
US 2020/0197102 A1    Jun. 25, 2020

Related U.S. Application Data

(60) Provisional application No. 62/539,291, filed on Jul. 31, 2017.

(51) Int. Cl.
*A61B 34/20*    (2016.01)
*A61B 34/10*    (2016.01)
*G06T 7/73*     (2017.01)
*G06T 19/00*    (2011.01)
*G06V 20/20*    (2022.01)

(52) U.S. Cl.
CPC .............. *A61B 34/20* (2016.02); *A61B 34/10* (2016.02); *G06T 7/74* (2017.01); *G06T 19/006* (2013.01);
(Continued)

(58) Field of Classification Search
CPC ... A61B 34/20; A61B 34/10; A61B 2034/107; A61B 2034/2051; A61B 2034/2055;
(Continued)

(56) References Cited

U.S. PATENT DOCUMENTS

2003/0179308 A1    9/2003    Zamorano et al.
2010/0134601 A1    6/2010    Lefevre et al.
(Continued)

FOREIGN PATENT DOCUMENTS

CN    108876725    *    5/2017    ............ G06T 5/006
WO    WO 2017/000988 A1    1/2017

OTHER PUBLICATIONS

International Search Report dated Oct. 16, 2018 in PCT/US2018/044604 filed on Jul. 31, 2018.
(Continued)

*Primary Examiner* — Rochelle D Turchen
(74) *Attorney, Agent, or Firm* — Oblon, McClelland, Maier & Neustadt, L.L.P.

(57) ABSTRACT

The present disclosure relates to a tracking system for augmented reality in a clinical setting. Specifically, the present disclosure relates to an approach for combining hardware-based tracking and computer vision-based tracking in order to accurately overlay a projected image onto a video image.

20 Claims, 13 Drawing Sheets

(52) U.S. Cl.
CPC ........ G06V 20/20 (2022.01); *A61B 2034/107* (2016.02); *A61B 2034/2051* (2016.02); *A61B 2034/2055* (2016.02); *A61B 2034/2065* (2016.02); *G06T 2207/20221* (2013.01); *G06V 2201/03* (2022.01)

(58) Field of Classification Search
CPC . A61B 2034/2065; G06T 7/74; G06T 19/006; G06T 2207/20221
See application file for complete search history.

(56) References Cited

U.S. PATENT DOCUMENTS

| | | |
|---|---|---|
| 2011/0216089 A1 | 9/2011 | Leung |
| 2012/0314942 A1 | 12/2012 | Williams et al. |
| 2013/0245461 A1 | 9/2013 | Maier-Hein et al. |
| 2014/0275760 A1 | 9/2014 | Lee et al. |
| 2014/0303491 A1* | 10/2014 | Shekhar ................. A61B 8/587 600/424 |
| 2016/0267659 A1 | 9/2016 | Vasey et al. |
| 2016/0302747 A1 | 10/2016 | Averbuch |

OTHER PUBLICATIONS

Written Opinion of the International Searching Authority issued in PCT/US2018/044604 filed on Jul. 31, 2018.

Lange et al., "Augmenting Intraoperative 3D Ultrasound with Preoperative Models for Navigation in Liver Surgery," International Conference on Medical Image Computing and Computer-Assisted Intervention, MICCAI 2004: Medical Image Computing and Computer-Assisted Intervention—MICCAI, 2004, pp. 534-541 (total 12 pages).

* cited by examiner

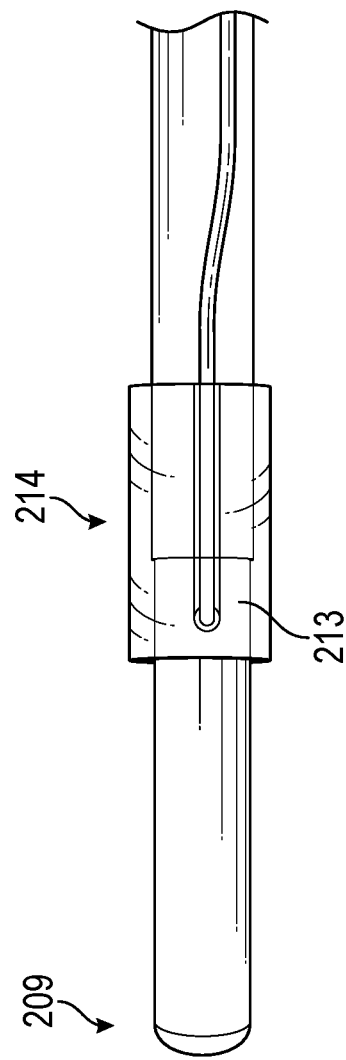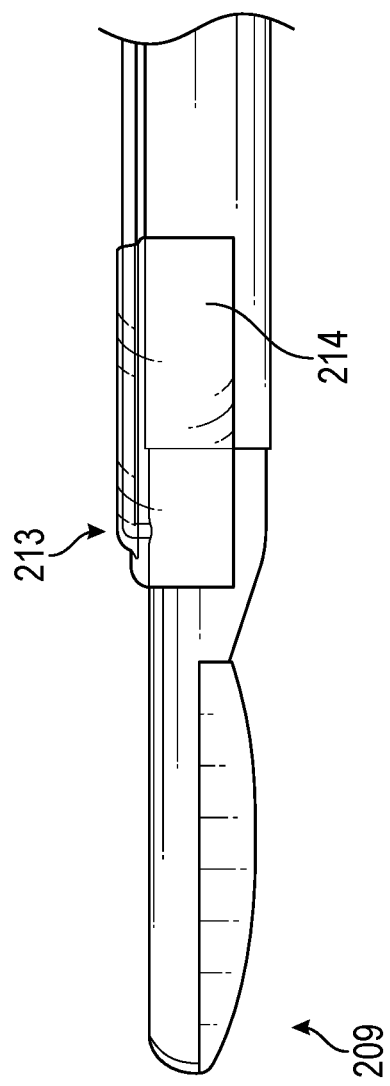

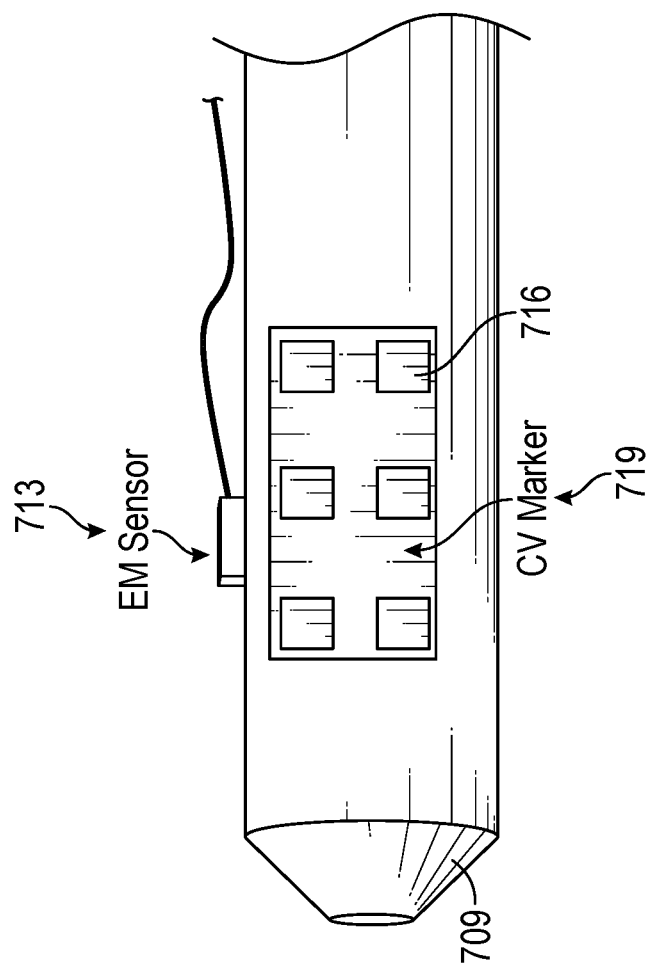

HYBRID HARDWARE AND COMPUTER VISION-BASED TRACKING SYSTEM AND METHOD

CROSS-REFERENCE TO RELATED APPLICATIONS

The present application claims priority to U.S. Provisional Application No. 62/539,291, filed Jul. 31, 2017, the teaching of which is hereby incorporated by reference in its entirety for all purposes.

GOVERNMENT LICENSE RIGHTS

This invention(s) was made with government support under 1R42CA192504 awarded by the National Institutes of Health (NIH). The government may have certain rights to the claimed invention(s)

BACKGROUND

Field of the Disclosure

The present disclosure relates to vision tracking systems, apparatuses, and methods, particularly hybrid, vision-based tracking systems, apparatuses, and methods for computer-assisted surgery.

Description of the Related Art

Laparoscopic augmented reality can improve a surgeon's experience of using multimodal visual data during a procedure by fusing of medical image data (e.g., ultrasound images) onto live laparoscopic video. Augmented reality studies based on only computer vision-based or only hardware-based (e.g., optical and electromagnetic tracking) approaches can introduce registration errors, for instance, because of variable operating conditions.

Laparoscopic surgery is an increasingly accepted mode of surgery because it is minimally-invasive and leads to much fast recovery and improved outcomes. In a typical laparoscopic surgery, the primary means of intraoperative visualization is a real-time video of the surgical field acquired by a laparoscopic camera. Compared to an open surgery, laparoscopic surgery may lack tactile feedback. Moreover, laparoscopic video can be capable of providing only a surface view of the organs and may not show anatomical structures beneath the exposed organ surfaces. One solution to this problem is augmented reality, a method of overlaying imaging data—in this instance, laparoscopic ultrasound imaging data—onto live laparoscopic video. This capability may be able to provide for improved surgical procedure planning, improved surgical tool navigation, and reduced procedure times.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to a tracking system, method, and computer-readable medium for augmented reality.

According to an embodiment, the present disclosure further relates to a tracking system for augmented reality, the tracking system comprising an imaging modality configured to obtain a medical image, a display configured to display the medical image, and an image control device including a processing circuitry configured to acquire spatial data of a real object, observed in the medical image of the imaging modality, via a first tracking method, determine a projection matrix based upon the acquired spatial data of the real object, project a virtual object onto the medical image of the imaging modality, the virtual object being a projection of the real object according to the projection matrix, calculate a correction matrix, update the projection of the virtual object according to the correction matrix, and modify the display of the medical image based on the updated projection.

According to an embodiment, the present disclosure further relates to a method for augmented reality, comprising acquiring, via processing circuitry, spatial data of a real object observed in a medical image of an imaging modality via a first tracking method, determining, via the processing circuitry, a projection matrix based upon the acquired spatial data of the real object, projecting, via the processing circuitry, a virtual object onto the medical image of the imaging modality, the virtual object being a projection of the real object according to the projection matrix, calculating, via the processing circuitry, a correction matrix, updating, via the processing circuitry, the projection of the virtual object according to the correction matrix, and displaying, via the processing circuitry, the medical image, wherein the displayed medical image is modified based upon the updated projection.

According to an embodiment, the present disclosure further relates to a non-transitory computer-readable storage medium storing computer-readable instructions that, when executed by a computer, cause the computer to perform a method of augmented reality, comprising acquiring spatial data of a real object observed in a medical image of an imaging modality via a first tracking method, determining a projection matrix based upon the acquired spatial data of the real object, projecting a virtual object onto the medical image of the imaging modality, the virtual object being a projection of the real object according to the projection matrix, calculating a correction matrix, updating the projection of the virtual object according to the correction matrix, and displaying the medical image, wherein the displayed medical image is modified based upon the updated projection.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 2A is a schematic of a superior view of an aspect of a laparoscopic ultrasound transducer, according to an exemplary embodiment of the present disclosure;

FIG. 2B is a schematic of a lateral view of an aspect of a laparoscopic ultrasound transducer, according to an exemplary embodiment of the present disclosure;

FIG. 7 is an illustration of a laparoscopic system including a user-defined pattern for computer vision-based tracking, according to an exemplary embodiment of the present disclosure;

DETAILED DESCRIPTION

Figure 1:
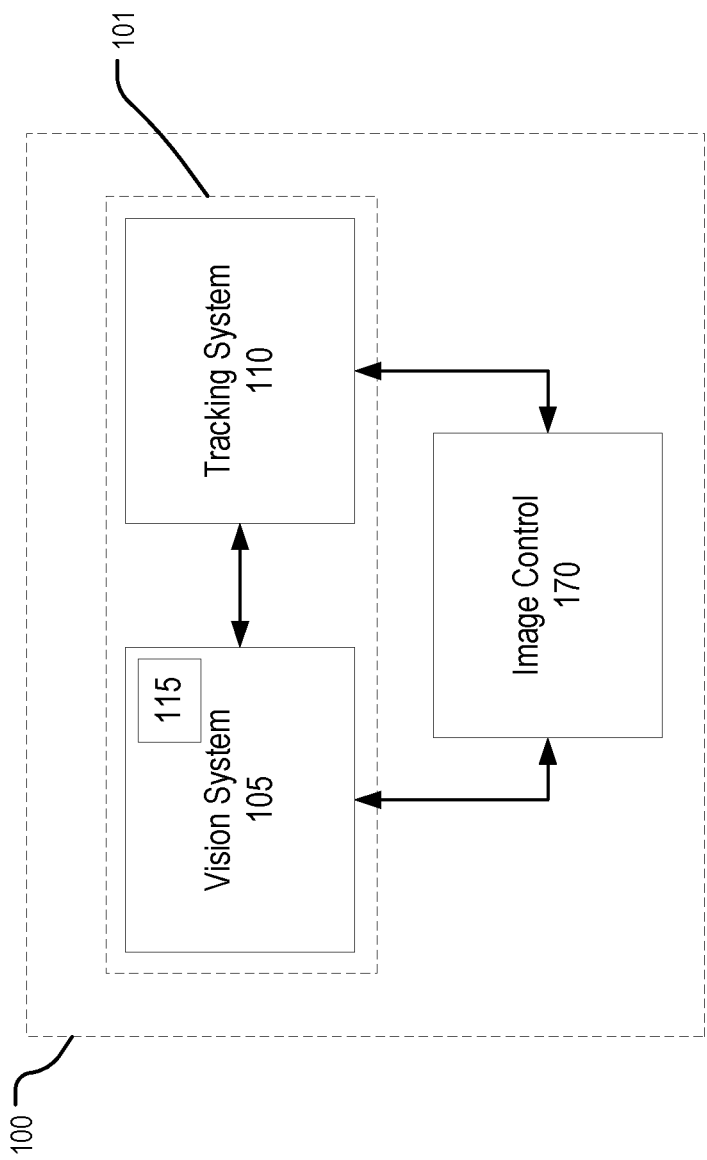
FIG. 1 is a block diagram of a clinical system, according to an exemplary embodiment of the present disclosure.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

Moreover, it should be appreciated that the terms "transducer" and "probe", as used in the Specification, appended Claims and Abstract, are used interchangeably to refer to a device that produces sound waves. Similarly, it should be appreciated that the terms "computer vision" and "CV", as used in the Specification, appended Claims and Abstract, are used interchangeably.

It must also be noted that, as used in the Specification, appended Claims and Abstract, the singular forms "a," "an," and "the" include plural referents unless the context clearly dictates otherwise. That is, unless clearly specified otherwise, as used herein the words "a" and "an" and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein, merely describe points of reference and do not necessarily limit embodiments of the described subject matter to any particular orientation or configuration. Furthermore, terms such as "first," "second," "third," etc. merely identify one of a number of portions, components, points of reference, operations and/or functions as described herein, and likewise do not necessarily limit embodiments of the described subject matter to any particular configuration or orientation.

A typical augmented reality approach may include registration of real-time laparoscopic ultrasound images onto live laparoscopic video, followed by their superimposition. To this end, image-to-video registration methods can be divided into two broad categories: (1) computer vision-based methods and (2) hardware-based methods.

Computer vision-based methods use computer vision techniques to track, in real time, natural anatomical landmarks, user-introduced patterns within the field of view of the camera used, and the like. As related to the above-described approaches, when ultrasound is the selected augmenting imaging modality, tracking the ultrasound transducer in a field of view is the goal. For example, some methods attach user-defined patterns on the ultrasound transducer and track those patterns in a video. Alternatively, other methods directly track the laparoscopic ultrasound transducer in a video by detecting lines describing the outer contours of the transducer probe. In both instances, however, computer vision-based approaches may degrade or fail in the presence of occlusion, variable lighting conditions, and the like.

Hardware-based methods employ external tracking hardware devices for real time tracking. Optical tracking, for instance, can use infrared cameras to track optical markers affixed rigidly on desired tools and imaging devices. Augmented reality systems based on electromagnetic tracking have also been proposed. In both instances, tracking hardware may be susceptible to two types of error: (1) system errors and (2) calibration errors. System-based errors in electromagnetic tracking can often stem from ferrous metals and conductive materials in tools that are in close proximity to a field generator, while optical markers may frequently suffer from a line of sight problem. Calibration-based registration errors could be associated with experimental errors generated during system calibration, which may include ultrasound calibration and laparoscopic camera calibration.

In light of the above-described deficiencies of independently-implemented tracking systems, the present disclosure is related to a hybrid tracking system employing both computer vision-based tracking and hardware-based tracking. Generally, according to an embodiment, the present disclosure relates to vision tracking systems, apparatuses, and methods, particularly to hybrid, vision-based tracking systems, apparatuses, and methods for computer-assisted surgery. Systems, apparatus, and methods according to one or more embodiments of the disclosed subject matter can implement both hardware-based tracking (e.g., electromagnetic and/or optical) and computer vision-based tracking (e.g., augmented reality and/or tool segmentation). Such hybrid tacking systems, apparatus, and methods can improve accuracy of augmented reality and/or mixed reality tracking. Additionally, or alternatively, according to an embodiment, the present disclosure further relates to real-time overlaying or merging of data from different types of tracking operations. Moreover, by leveraging both computer vision-based tracking and hardware-based tracking, embodiments of the present disclosure may provide redundant capabilities, thus increasing robustness.

Specifically, according to an embodiment, the present disclosure is related to the combination of electromagnetic-based tracking and computer vision-based tracking, wherein, after registering an ultrasound image and overlaying the ultrasound image, via an electromagnetic-based approach on a time-matched video frame, the computer vision-based approach is implemented to refine the registration and subsequent fusion. Thus, according to an embodiment, the present disclosure is related to hybrid tracking for improved registration of laparoscopic ultrasound and laparoscopic video for augmented reality. In another embodiment, the present disclosure is related to systems, apparatuses, and methods for registering an ultrasound image with a time-matched video frame using electromagnetic tracking followed by a computer vision-based refinement of the registration and subsequent fusion. Such a rectified calibration method can be accomplished in two stages by: (1) computing a correction transformation which when applied to a 3D computer aided design model of the laparoscopic ultrasound transducer probe improves the alignment of its projection with the actual laparoscopic ultrasound transducer probe visible in the camera image and (2) incorporating the calculated correction transformation in the overall calibration system.

According to an embodiment, the present disclosure is related to a hybrid tracking method comprising both hardware-based and computer vision-based methods for providing consistent, accurate and reliable image fusion for an augmented reality system. The above described hardware-based component of the hybrid tracking system can include, for example, electromagnetic tracking of a laparoscopic ultrasound transducer with a flexible imaging tip. According to an embodiment, the same framework can also be applied to optical tracking, additionally or alternatively.

Of course, embodiments of the present disclosure are not so limited, and can be used for any tracked tool in a computer-assisted surgical setup in which the spatial location of the surgical tool may be pertinent to the observation (e.g., needle trajectory, target fiducials, pill cameras, etc.) and outcome of a procedure.

With reference now to FIG. 1, and according to an embodiment of the present disclosure, a clinical system 100 may be an augmented reality (AR) system, method, and apparatus including a clinical vision system 105 comprising a computer vision-based tracking system 115, a hardware-based tracking system 110, and an image control device 170. In an embodiment of the clinical system 100, the clinical vision system 105 can be a clinical vision system 105 including an endoscope and a medical imaging modality. The endoscope can be a 10-mm 0° laparoscope with a camera and the medical imaging modality can be an ultrasound system comprising an ultrasound scanner and a 9-mm laparoscopic ultrasound (LUS) transducer with, for instance, a flexible imaging tip. In an embodiment, the hardware-based tracking system 110 can be an electromagnetic (EM) tracking system, an optical tracking system, and the like. Wherein the hardware-based tracking system 110 is an EM tracking system, the EM tracking system is concurrently operated with a tabletop field generator that establishes an EM tracking volume. Together, the hardware-based tracking system 110 and the computer vision-based tracking system 115 of the clinical vision system 105 comprise a hybrid tracking system 101. In an embodiment, the image control device 170 is a graphics processing unit-accelerated laptop computer that runs image fusion software. In another embodiment, the image control device 170 is a computer, as described below in FIG. 13.

According to an embodiment, each component of the clinical system 100, including the hardware-based tracking system 110, the image control device 170, and the computer vision-based tracking system 115 of the clinical vision system 105 are configured for data communication with each of the other components of the clinical system 100. In an embodiment, a display is integrally constructed within the image control device 170 for visual communication of processed, communicated data, or medical images, from the clinical system 100. In another embodiment, the display is electrically-coupled to the image control device 170 for visual communication the processed, communicated data, or medical images, from the clinical system 100.

As it relates to the EM tracking system of the hardware-based tracking system 100, and with reference now to FIGS. 2A and 2B, wherein FIG. 2A is a superior view and FIG. 2B is a lateral view, the system, apparatus, or method can include an EM sensor mount 214, removably-coupled to a distal end of a LUS transducer 209, to hold an EM sensor 213 of the EM tracking system. According to an embodiment, the EM sensor 213 can be delivered to the EM sensor mount 214 via a biopsy needle introducer track within the LUS transducer 209. In an example, the EM sensor mount 214 can be a wedge-shaped EM sensor mount. In another example, the EM sensor mount 214 can be minimally larger than a diameter of the LUS transducer 209 such that the LUS transducer 209, with attached EM sensor mount 214, can be slidably moved within, for instance, a 12-mm trocar or other typically-sized trocar for use with the LUS transducer 209. In an example, the EM sensor mount 214 is fabricated from a material selected from a group including polystyrene, poly(methyl methacrylate), polyethylene, polyurethane, polyethylene terephthalate, polytetrafluoroethylene, polysulfone, and the like, via a method selected from a group including milling, machining, extruding, thermoforming, 3D printing, and the like.

Figure 3:
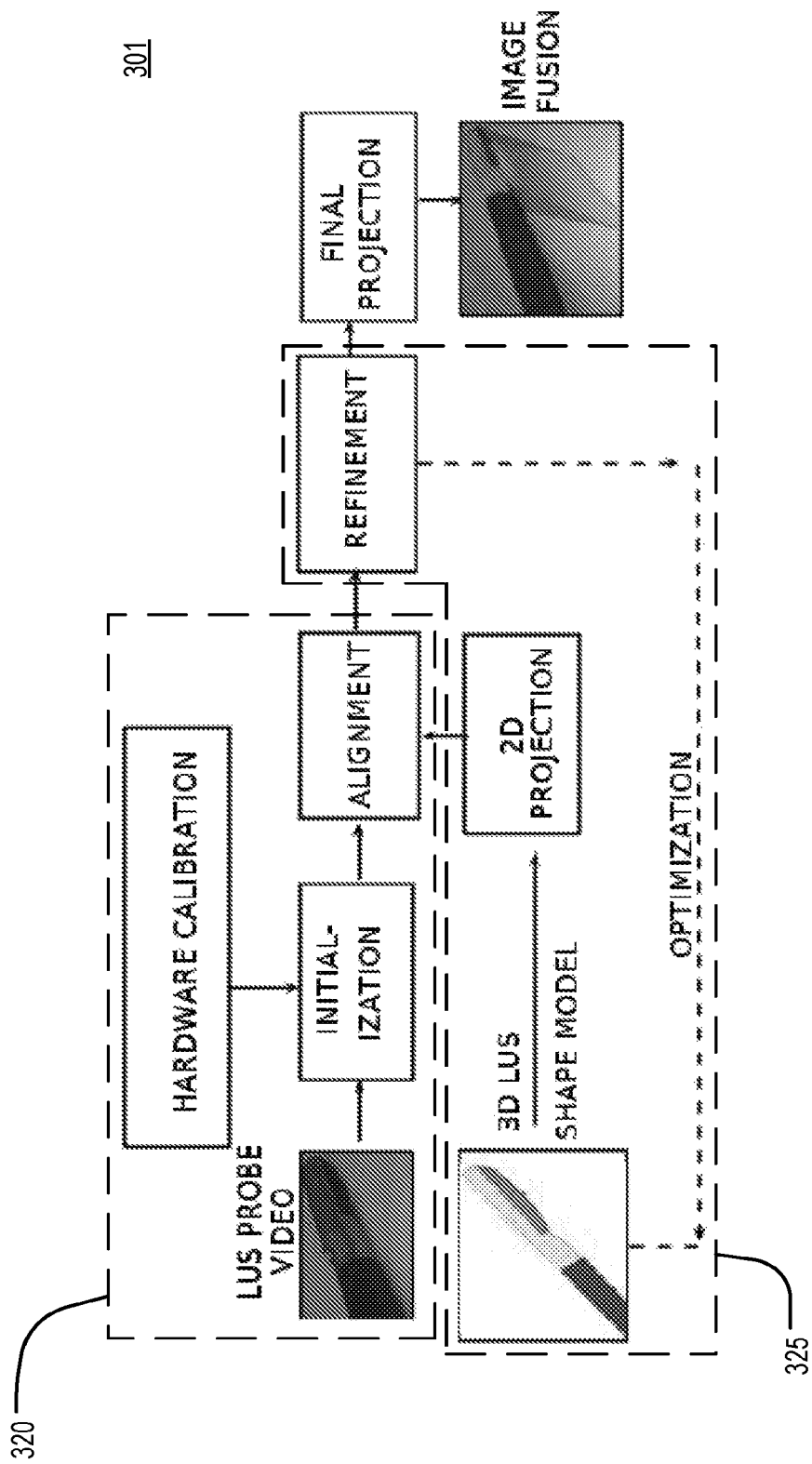
FIG. 3 is a flowchart of a hybrid tracking approach, according to an exemplary embodiment of the present disclosure.

FIG. 3 is an exemplary flowchart of an aspect of a system or apparatus of the present disclosure, according to an embodiment. Generally, the system or apparatus can have two main stages performed by the image control device. A first stage 320 can be comprised of two sub-stages that can perform specific functions or operations. In a first sub-stage, a calibration of the AR system components, including a laparoscope producing a camera image and a LUS transducer producing an LUS image is computed. In a second sub-stage, the LUS image, or, for instance, the LUS transducer of the LUS image, a real object, is registered with the camera image, or, for instance, a 2D projection of a 3D LUS transducer model, a virtual object, the registration being displayed on the camera image using the computed calibration results. In a second stage 325, a virtual model of the LUS transducer model, the virtual object, can be optimally fitted to a corresponding real object, or LUS transducer, visible within the camera image. In achieving this, position and pose parameters of the 3D LUS transducer model can be optimized to determine a best fit of the virtual object to the real object within the camera image. The subsequently required action in order to achieve the optimization is a correction transformation matrix, or correction matrix. The correction matrix can be fed back into the first stage 320 and, thus, the registration of the virtual object to the real object within the camera image can be refined. In an embodiment, the camera image may be a video.

System Calibration

Let $p_{US}=[x\ y\ 0\ 0]^T$ denote a point in the LUS image in homogeneous coordinates, in which the z coordinate is 0. Further, let $p_{Lap}^U=[u\ v\ 1]^T$ denote the point that $p_{us}$ corresponds to in the undistorted camera image. When $T_A^B$ is denoted as a 4×4 transformation matrix from a coordinate system of A to that of B, the registration of $p_{US}$ on the undistorted camera image can be expressed as $$p_{Lap}^U = C \cdot [I_3 0] \cdot T_{Mark-Lap}^{Cam} \cdot T_{Tracker}^{Mark-Lap} \cdot T_{Mark-US}^{Tracker} \cdot T_{US}^{Mark-US} \cdot p_{US} \quad (1)$$

where US refers to the LUS image, Mark-US refers to the EM sensor attached to the EM sensor mount on the LUS transducer, Tracker refers to the EM tracking system, Mark-Lap refers to the EM sensor attached on the laparoscope, Cam refers to the laparoscopic camera, $I_3$ is an identity matrix of size 3, and C is the camera matrix. Moreover, $T_{US}^{Mark-US}$ can be obtained from ultrasound calibration, $T_{Mark-US}^{Tracker}$ and $T_{Tracker}^{Mark-Lap}$ can be obtained from the EM sensor tracking system, and $T_{Mark-Lap}^{Cam}$ and C can be obtained from the laparoscopic calibration.

Improved System Calibration

To refine the registration of the LUS image, the 3D LUS transducer model, or virtual object, can be first projected on the camera image using the standard calibration results, as referenced at No. 320 in FIG. 3. A computer vision-based approach can then be applied to register the projected virtual object with the actual LUS transducer, or real object, shown in the video. This can yield a correction matrix $T_{Corr}$ as a rigid transformation. Since there can be a fixed geometric relationship between the LUS transducer and the LUS image, the same $T_{Corr}$ can be used to refine the location of the LUS image overlaid on the video. As an update to Eq. (1), a summary of the above-described approach can be expressed as $$p_{Lap}^U = C \cdot [I_3 0] \cdot T_{Corr} \cdot T_{Mark-Lap}^{Cam} \cdot T_{Tracker}^{Mark-Lap} \cdot T_{Mark-US}^{Tracker} \cdot T_{US}^{Mark-US} \cdot T_{Model}^{US} \cdot p_{Model} \quad (2)$$

where points of the 3D LUS transducer model are first transferred to the LUS image coordinate system through $T_{Model}^{US}$ in Eq. (2).

LUS Probe Model and Calibrations

Figure 4B:
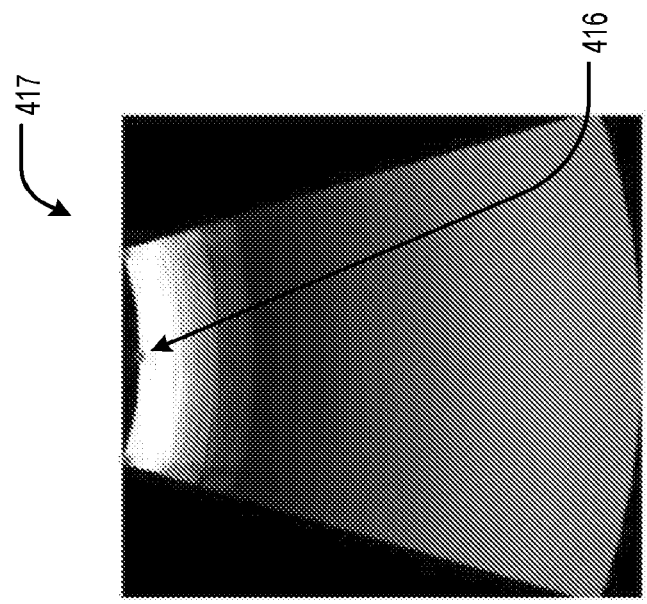
FIG. 4B is an illustration of a laparoscopic ultrasound image, according to an exemplary embodiment of the present disclosure.
Figure 4A:
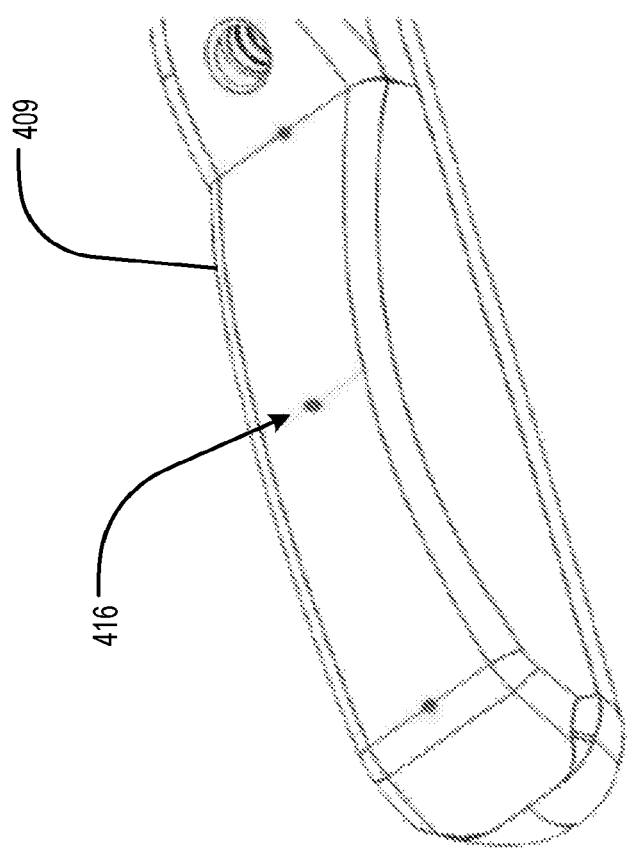
FIG. 4A is a schematic of a hardware-based aspect of a laparoscopic ultrasound transducer computer-aided design model, according to an exemplary embodiment of the present disclosure.

A 3D computer aided design model of an LUS transducer can be obtained. In an embodiment, the exact geometric relationship between an imaging tip of the LUS transducer and an LUS image acquired therefrom is a fixed relationship as determined by a manufacturer of the LUS transducer. In an example, the fixed relationship can be acquired from the manufacturer of the LUS transducer. In another example, the fixed geometric relationship between the imaging tip of the LUS transducer and the LUS image can be determined via a simple registration operation that can be implemented to transfer the coordinate system of the computer aided design model to that of the LUS image (assuming the LUS image space is 3D with z=0). As illustrated in FIG. 4A and FIG. 4B, and in order to allow computer vision-based tracking, an LUS transducer 409 can be outfitted with one or more characteristic points 416. The one or more characteristic points 416 can be formed integrally with the LUS transducer 409 or can be affixed to the LUS transducer 409. In an example, the one or more characteristic points 416 are three characteristic points 416, as depicted in FIG. 4A. Employed for tracking the LUS transducer 419 within an LUS image 417, a corresponding location of each of the one or more characteristic points 416 is depicted in FIG. 4B. According to an embodiment, a scan depth can be set in accordance with a tissue volume of interest. In an example, and without loss of generality, the scan depth of the LUS image can be to 6.4 cm, a depth setting commonly used for abdominal procedures. A simple three-point rigid registration can then be performed to obtain $T_{Model}^{US}$ in Eq. (2).

Ultrasound calibration can be performed using the tools provided in the PLUS library, an open-source toolkit for ultrasound-guided intervention systems. Laparoscope calibration can then be performed using a so-called "fast approach" which requires only a single image of the calibration pattern.

According to an embodiment, the above-described calibration and registration can be improved via inclusion of an identifying marker on the LUS transducer. In an example, the identifying marker is a QR-code communicating transducer type. In another example, the identifying marker is used for immediate registration of pose and position of the LUS transducer, which may subsequently be used for alignment.

Model Projection and Alignment—Computer Vision-Based Feature Extraction

Figure 5:
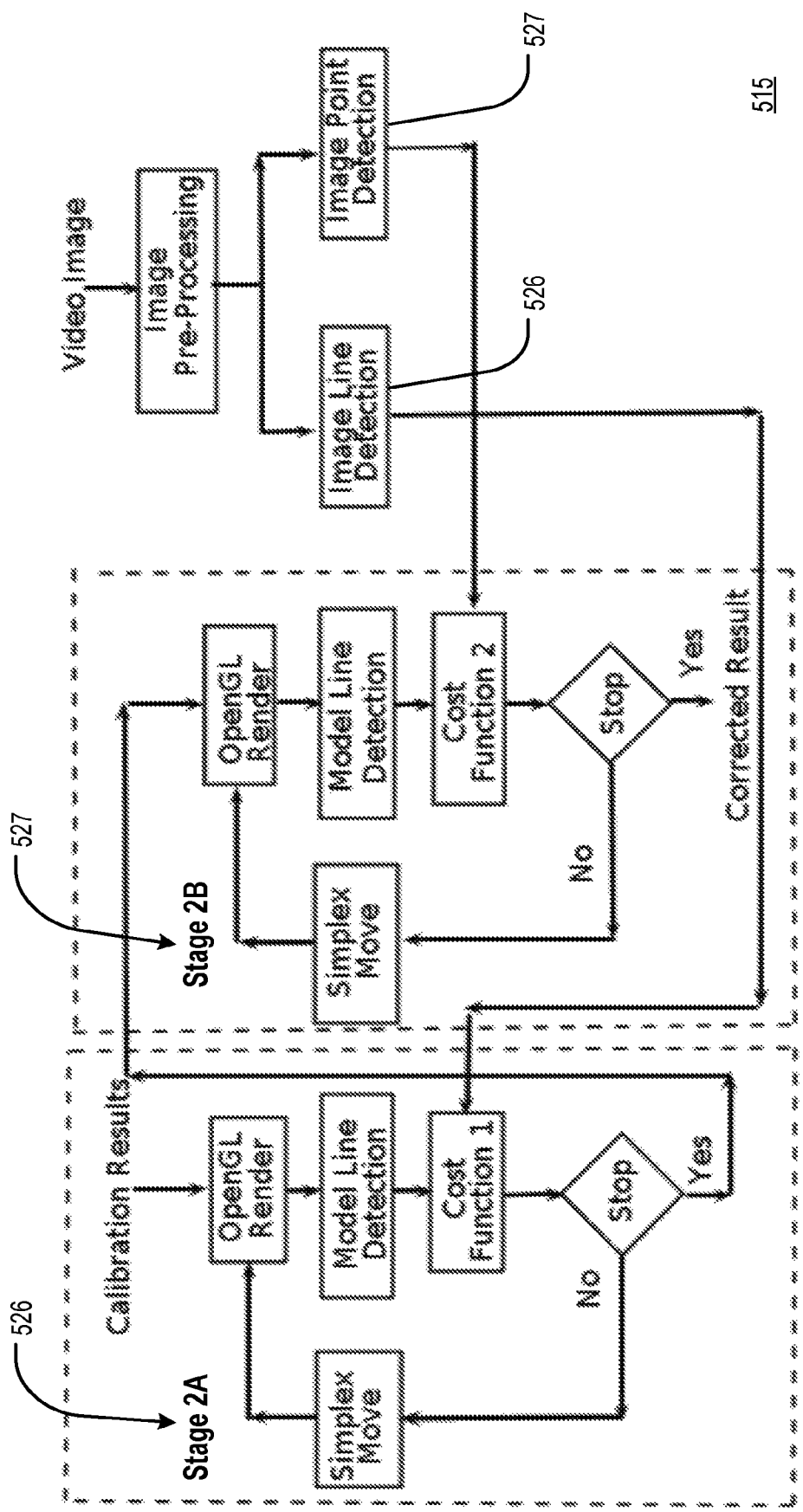
FIG. 5 is a flowchart of a computer vision-based refinement approach, according to an exemplary embodiment of the present disclosure.

To compare the pose and position of the rendered virtual model of the transducer and the transducer in the camera image, a computer vision-based refinement workflow of a computer vision-based tracking system 515, described in FIG. 5, can be implemented. The below-described hybrid approach and workflow is non-limiting example of a computer vision-based object tracking workflow and, therefore, is merely exemplary of a variety of approaches for computer vision-based object tracking.

Figure 6A:
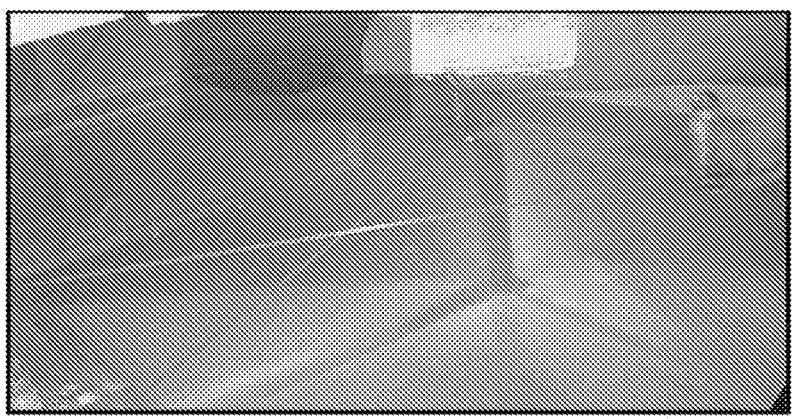
FIG. 6A is an intermediate result determined according to a hybrid tracking system, according to an exemplary embodiment of the present disclosure.
Figure 6B:
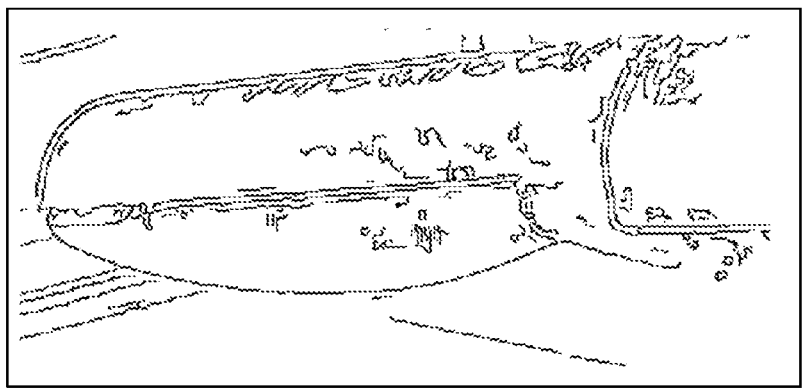
FIG. 6B is an intermediate result determined according to a hybrid tracking system, according to an exemplary embodiment of the present disclosure.
Figure 6C:
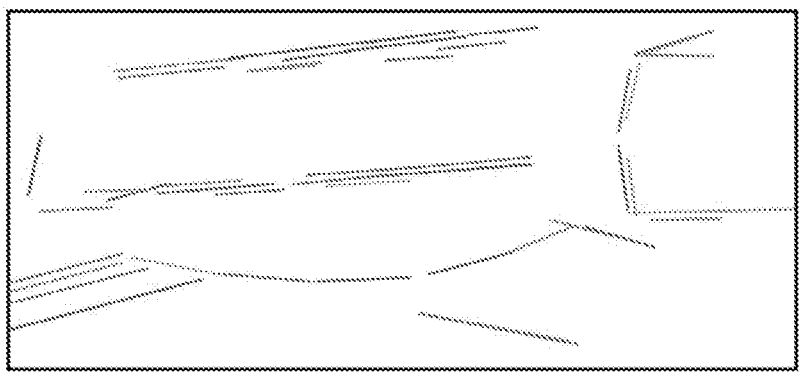
FIG. 6C is an intermediate result determined according to a hybrid tracking system, according to an exemplary embodiment of the present disclosure.
Figure 6D:
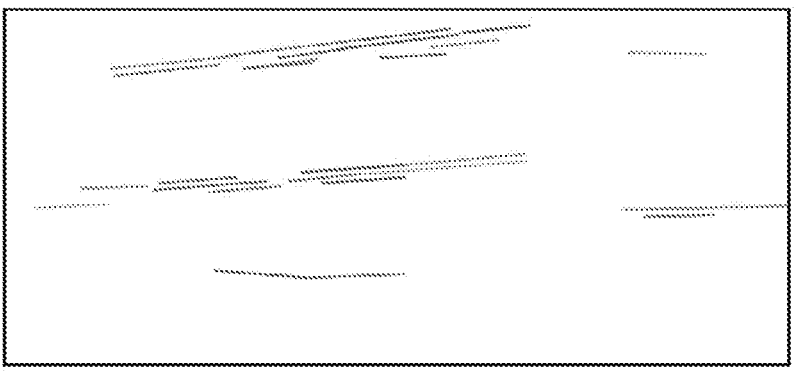
FIG. 6D is an intermediate result determined according to a hybrid tracking system, according to an exemplary embodiment of the present disclosure.

To this end, the computer vision-based object tracking workflow of the present disclosure describes a workflow for image line detection 526 and image point detection 527 following image pre-processing of a video image. First, a region of interest (ROI) can be generated for each frame of a first imaging modality using fast visual tracking based on robust discriminative correlation filters such that subsequent processing focuses on the imaging tip, as shown at No. 618 in FIG. 6A. Based on this coarse estimate of the probe's location, the bounding box surrounding the imaging tip can be intended to include at least some portion of the top, middle, and tip of the transducer as seen by the camera. In order to find the straight edges of these features of the transducer, the image can first be converted to a gray scale image based on brightness, followed by Canny edge detection, for instance, as shown in FIG. 6B. A Probabilistic Hough Transform (PHT) can be used to extract a first set of lines from the edge detection result within the ROI, an example of which is shown in FIG. 6C. As shown in FIG. 6D, the first line set can be filtered, for instance, by creating a coarse grain 2D histogram with the axes defined by PHT parameters (r, θ; magnitude and direction) and values of the histogram defined by the sum of the lengths of lines in the bin. All lines not contained within the highest peak present in the 2D histogram, therefore, can be removed to generate a second set of lines that corresponds with the long edges and is substantially parallel to an object of interest, which may be a projection of a transducer, or virtual object, or an actual transducer, or real object, according to the imaging modality. From this smaller, second set of lines, a fine grain 2D histogram, based on the PHT parameters (r, θ; magnitude and direction), can be created. The two highest peaks in this histogram, determined to be the longest lines, may represent the top and middle of the transducer of either the projection of the transducer or the actual transducer, and be selected. The indices of the peaks, defining the ROI of the first imaging modality, can then be used in one of at least one cost function for the optimization of the virtual object location. Similarly, the same procedure to detect a corresponding two feature lines for a second imaging modality can be performed. In an example, the first imaging modality can be ultrasound and the second imaging modality can be laparoscopic video.

According to an embodiment, the above-described line feature extraction can be performed via PHT, as described above, or via custom designed markers including AR marker, checkerboard marker, dot marker, and the like, and machine learning-based binary segmentation of the tool including, among others, convolutional neural networks.

With reference again to FIG. 5 and according to an embodiment, in Stage 2A 526 of optimization, alignment of extracted feature lines are compared. The alignment of the feature lines may be compared using a cost function defined as $$F_1(x) = \sum_{i=1}^{2}[w_r \cdot (r_{img}^i - r_{gl}^i(x))^2 + w_\theta \cdot (\theta_{img}^i - \theta_{gl}^i(x))^2] \quad (3)$$

where w is a scalar, img refers to the camera image, and gl refers to the OpenGL-rendered 3D LUS transducer model. In an embodiment, the above-described optimization employs a linear programming method to determine a best outcome by searching for the five parameters x associated with a rigid transformation ($T_{Corr}$ in Eq. (2)). In an example, the linear programming method is a simplex method. In an embodiment of the present disclosure, a parameter associated with rotation about the LUS transducer axis may be fixed. Only considering two feature lines as constraints, however, the optimization in Stage 2A 526 may not accurately estimate parameters associated with translation along the LUS transducer axis.

To this end, and as described in Stage 2B 527 of optimization, corresponding feature points of a first imaging modality and a second imaging modality can be detected to address any inaccuracies along the LUS transducer axis. First, a gradient descent-based active contours method, or snakes segmentation, can be performed to segment corresponding regions of interests from the first imaging modality and the second imaging modality. In an example, segmentation isolates the LUS transducer within the object projection and within the laparoscopic video such that a feature point, p, defined as the farthest point corresponding with the tip of the LUS transducer (virtual object or real object), can be selected. The initialization for segmentation can be provided by an ellipse encompassing the ROI. The corresponding feature points can be compared using another cost function expressed as $$F_2(x) = w_p \cdot d(p_{img}, p_{gl}(x))^2 \quad (4)$$

where d(·, ·) is the Euclidean in an image. In Stage 2B 527 of the optimization, a simplex search, or similar optimization approach, may be restricted to focus on only one of the six parameters or, for example, the one associated with translation along the LUS transducer axis, wherein the remaining five parameters are held constant at their results from Stage 2A 526 of the optimization.

In an embodiment, the resulting outputs of the above-described simplex searches yield a correction matrix that can be applied to the projection of the LUS transducer within the camera image. Further, calculation of the correction matrix via the above-described feature extraction and optimization method can be performed iteratively until a performance threshold is met, or at pre-determined intervals such that the projection of the LUS transducer within the camera image may be updated. In updating the calculation of the correction matrix, the projection of the LUS transducer, or virtual object, and the LUS image therefrom, can accurately track in a surgical field.

According to an embodiment, for both stages of optimization, the simplex search can be terminated based upon a comparison of a current value of a cost function and the tolerances set on both input and cost function deltas.

According to an embodiment of the preset disclosure, following hardware-based AR visualization via C++ on a GPU-accelerated laptop computer, image control device, or the like, the above-described computer vision-based refinement approach can be implemented via OpenCV and scikit-image in Python, for example. In an embodiment, the Python-based refinement implementation utilizes internal APIs with the C++ based AR code base to transfer images and results between the two.

Model Projection and Alignment—Computer Vision-Based Feature Detection

According to an embodiment, and as an alternative to the line and tip feature extraction method described above, the present disclosure describes a computer vision-based feature detection method. With reference to FIG. 7, the computer vision-based feature detection method, executable by a processing circuitry, or image control device, comprises detecting the presence of a computer vision marker 719. The computer vision marker 719 can be a user-defined pattern including one or more characteristic points 716. In an embodiment, the computer vision marker 719 can be a checkerboard pattern including black squares on a white background or similarly contrasting, user-defined pattern, such that the user-defined pattern is easily detectable by a computer vision-based feature detection method, as would be understood by one of ordinary skill in the art. The computer vision marker 719 can be affixed to or formed integrally with a surgical tool or, for instance, an LUS transducer 709. The LUS transducer 709 can further comprise an EM sensor 713, wherein a first projection of a model of the LUS transducer 709 is generated with data acquired from the EM sensor 713. In an embodiment, detection of the computer vision marker 719 can be performed for both the EM sensor-based projection of the model of the LUS transducer 709 and the LUS transducer 709 as observed in the camera image.

According to an embodiment, having detected the computer vision marker 719 and identified the LUS transducer 709 in the EM sensor-based projection and in the camera image, a correction matrix can be calculated based upon the malalignment of the projection of the model of the LSU transducer 709, or virtual object, and the LUS transducer in the camera image, or real object. In an embodiment, calculation of the correction matrix via the above-described feature detection method can be performed iteratively at pre-determined intervals such that the projection of the LUS transducer 709 within the camera image may be updated longitudinally and the LUS image, therefrom, can accurately track in a surgical field.

Model Projection and Alignment—Machine Learning-Based Feature Classification

According to an embodiment, and as another alternative to the line and tip feature extraction method described above, the present disclosure describes a machine learning-based feature classification approach to identification of a real object or, in an example, a LUS transducer. Generally, a machine learning-based framework, executable by a processing circuitry, or image control device, can be used to receive one or more images from one or more inputs and to process, analyze, and predict a classification of at least one object of interest within the one or more images. In an embodiment, the at least one object of interest within the one or more images can be a real object, or LUS transducer, within a camera image. In another embodiment, the at least one object of interest can be a virtual object, or a projection of a 3D LUS transducer model. Specifically, the machine learning-based framework can employ a machine learning algorithm, trained via supervised learning, including, among others, support vector machines, neural networks, deep learning, feature selection, and learning classifier systems. In an example, the machine learning-based framework is a fully convolutional neural network.

According to an embodiment, the machine learning method, and classifier therein, can be trained on a training database of ground truth data related to each of the at least one object of interest including, among others, data describing a shape and texture of a LUS transducer or data describing a computer vision marker. In an example, the training database, and ground truth data, therein, can include data describing a shape and texture of a LUS transducer within one or more camera images, including per-pixel labels describing the real object. The per-pixel labeling of the real object facilitates direct matching with the virtual object such that a correction matrix or direct tracking data can be obtained in camera space. It can be appreciated that per-pixel labels, wherein per-pixel labels describe the real object such that it can be matched to the virtual object, are merely exemplary of an approach employing a fully convolutional neural network and are non-limiting.

In other words, the data related to the each of the at least one object of interest within the one or more camera images of the ground truth data can include real object reference data and virtual object reference data. According to an embodiment, following training, the machine learning method can be evaluated with testing data prior to implementation within clinical data, writ large, to ensure the quality of the predictions of the machine learning method. For instance, in identifying a spatial location of a virtual object, a projection of a 3D LUS transducer model, and a real object, a LUS transducer, the machine learning method can predict the presence and location of each of the above-described objects, from which a transformation between the real object and the virtual object can be determined.

In an embodiment, if it is determined, following testing, that the machine learning method fails to accurately predict the classification of the testing data, additional ground truth data can be added to the training database to improve the classification of the machine learning method. According to an embodiment, the machine learning method can include one or more classifiers corresponding to each of one or more classifications including real object, virtual object, and the like.

According to an embodiment, following testing of the machine learning method, the method may be implemented with experimental data. Following implementation, and per-pixel classification indicating the presence and position of virtual objects and real objects, the determined spatial relationship can be used to calculate a correction matrix to bring the virtual object into agreement with the real object. In an embodiment, calculation of the correction matrix via the above-described feature classification method can be performed iteratively at pre-determined intervals such that the projection of the 3D LUS transducer model within the camera image may be updated longitudinally.

Machine Learning-Based Tracking

According to an embodiment of the present disclosure, and as an alternative to the above-described feature extraction and refinement approach, a machine learning-based framework can be used to integrate, process, analyze, and synthesize a single tracking solution for an object of interest. Generally, the machine learning-based framework may be configured to receive data from one or more data inputs, determine a reliability value of each of the one or more data inputs, and, based upon the determined reliability value of each of the one or more data inputs, fuse the received reliable data from each of the one or more data inputs into a single data output reflecting a spatial change of the object of interest being tracked. In an embodiment, the one or more data inputs can be one or more sensors. Specifically, the machine learning-based framework can employ a machine learning method, trained via supervised learning, including, among others, support vector machines, neural networks, deep learning, feature selection, and learning classifier systems. In an example, the machine learning-based framework can be a neural network.

Figure 8:
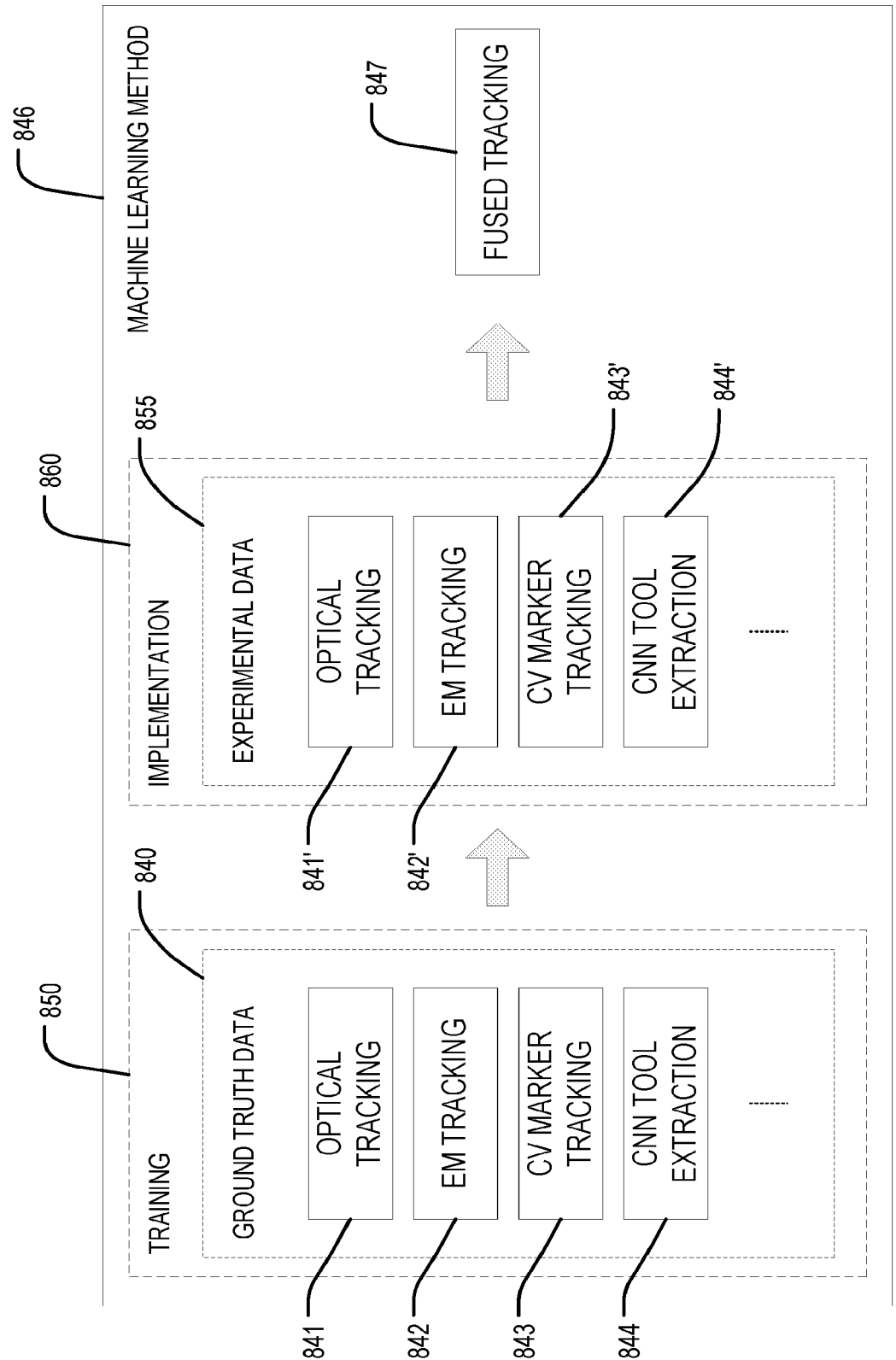
FIG. 8 is a flowchart of a machine learning-based hybrid approach, according to an exemplary embodiment of the present disclosure.

With reference to FIG. 8, the machine learning method 846, and classifier therein, can be trained 850 on a training database of ground truth data 840. The training database, and ground truth data 840, therein, can include data related to each of one or more data inputs, or one or more sensors, the one or more data inputs including optical tracking 841, EM tracking 842, computer vision marker tracking 843, convolutional neural network tool extraction 844, and the like. It can be appreciated that the number of data inputs described herein is merely exemplary and is non-limiting. Data obtained from computer vision marker tracking 843 and from the convolutional neural network tool extraction 844 can include location and orientation in 3D space via six degrees-of-freedom tracking data. In an example, the one or more sensors can include raw video images.

Moreover, the data related to each of the one or more data inputs can include positive reference data and negative reference data, wherein positive reference data is absent of artifacts that may degrade the reliability of the data input, including, among others, blurring and occlusions. In an example, a negative reference data of a data input from optical tracking 841 can include occlusion of a computer vision marker from a camera. In another example, a negative reference data of a data input from EM tracking 842 can include degradation of the data input by magnetic field distortion from other tools in the surgical field. According to an embodiment, following training, the machine learning method 846 can be evaluated with testing data prior to implementation within clinical data, writ large, to ensure the quality of the predictions of the machine learning method 846. For instance, in identifying a spatial location of a LUS transducer, or virtual object, using a data input from EM tracking, the machine learning method 846 can predict the presence of a degrading feature, such as magnetic field distortion, and classify the data input accordingly, thus removing the data input from its contribution to the final output. If it is determined, following testing, that the machine learning method 846 fails to accurately predict the classification of the testing data, additional ground truth data 840 can be added to the training database to improve the classification of the machine learning method 846. According to an embodiment, the machine learning method 846 can include one or more classifiers related to each of the one or more data inputs.

According to an embodiment, following testing of the machine learning method 846, the method may be implemented 860 with experimental data 855 from one or more data inputs. The one or more data inputs can include optical tracking 841', EM tracking 842', computer vision marker tracking 843', convolutional neural network tool extraction 844', and the like. For each of the one or more data inputs, the machine learning method 846 can determine a classification of the data input based upon the training 850, wherein the trained classifier determines the reliability of the data input based upon the presence or absence of artifacts. Subsequently, data inputs determined to be reliable are fused 847 into a singular output reflecting the tracking, and spatial orientation therein, of an object of interest.

Figure 9:
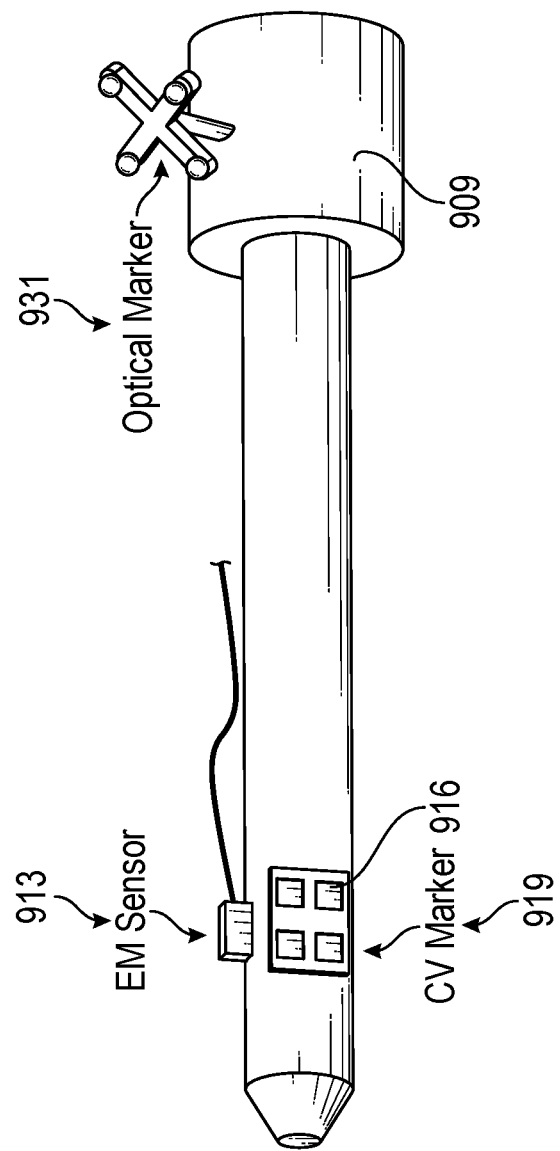
FIG. 9 is an illustration of a laparoscopic system including one or more sensors for a machine learning-based hybrid approach, according to an exemplary embodiment of the present disclosure.

According to an embodiment, FIG. 9 is an illustration of an object of interest of the present disclosure. In an embodiment, the object of interest can be a LUS transducer 909. To enable tracking of the LUS transducer 909 in the surgical field, one or more sensors, or data inputs, are affixed to the LUS transducer 909. The one or more sensors can include an EM sensor 913, an optical marker 931, and a computer vision marker 919 including one or more characteristic points 916.

Figure 10:
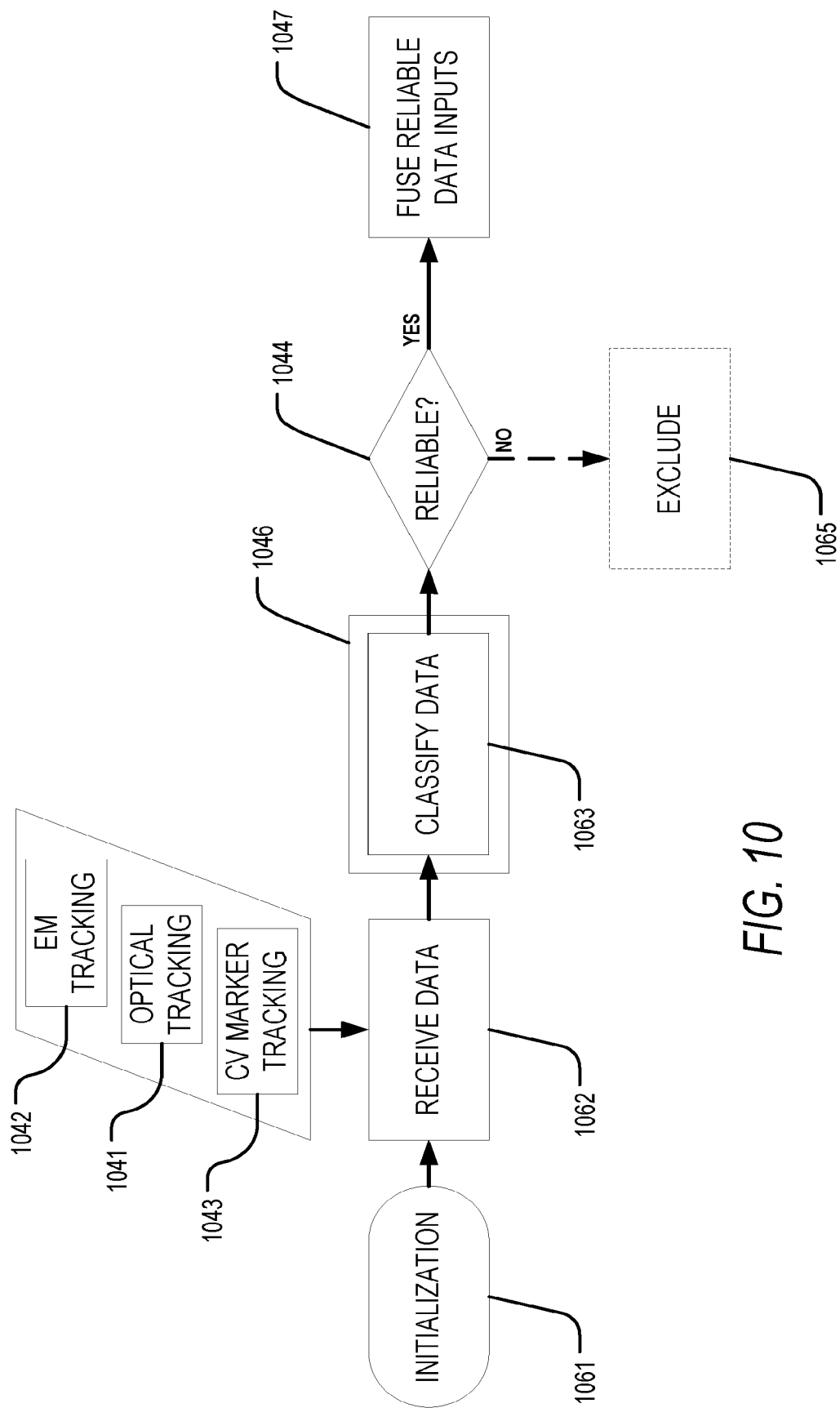
FIG. 10 is a flowchart of an implementation of a machine learning-based hybrid approach, according to an exemplary embodiment of the present disclosure.

Each of the one or more sensors described in FIG. 9 can be considered in context of the flowchart of FIG. 10. First, following initialization 1061 of a tracking system, data from one or more data inputs can be received 1062 by an image control device. The one or more data inputs can include EM tracking 1042, optical tracking 1041, and computer vision marker tracking 1043. Having received data 1062 from the one or more data inputs, the image control device can perform a machine learning method 1046 comprising classification 1063 of each of the one or more data inputs. Classification 1063 of each of the one or more data inputs can include determining the reliability of each, wherein the reliability of data from each, including EM tracking 1042, optical tracking 1041, and CV marker tracking 1043, can be degraded by artifacts. If classified reliable 1044, a data input can be included into a fused data output 1047 comprising other reliable data inputs. If classified unreliable 1044, the unreliable data input can be excluded 1065 from the fused tracking of the fused data output 1047.

Non-Limiting Experimental Information

Figures 11A, 11B:
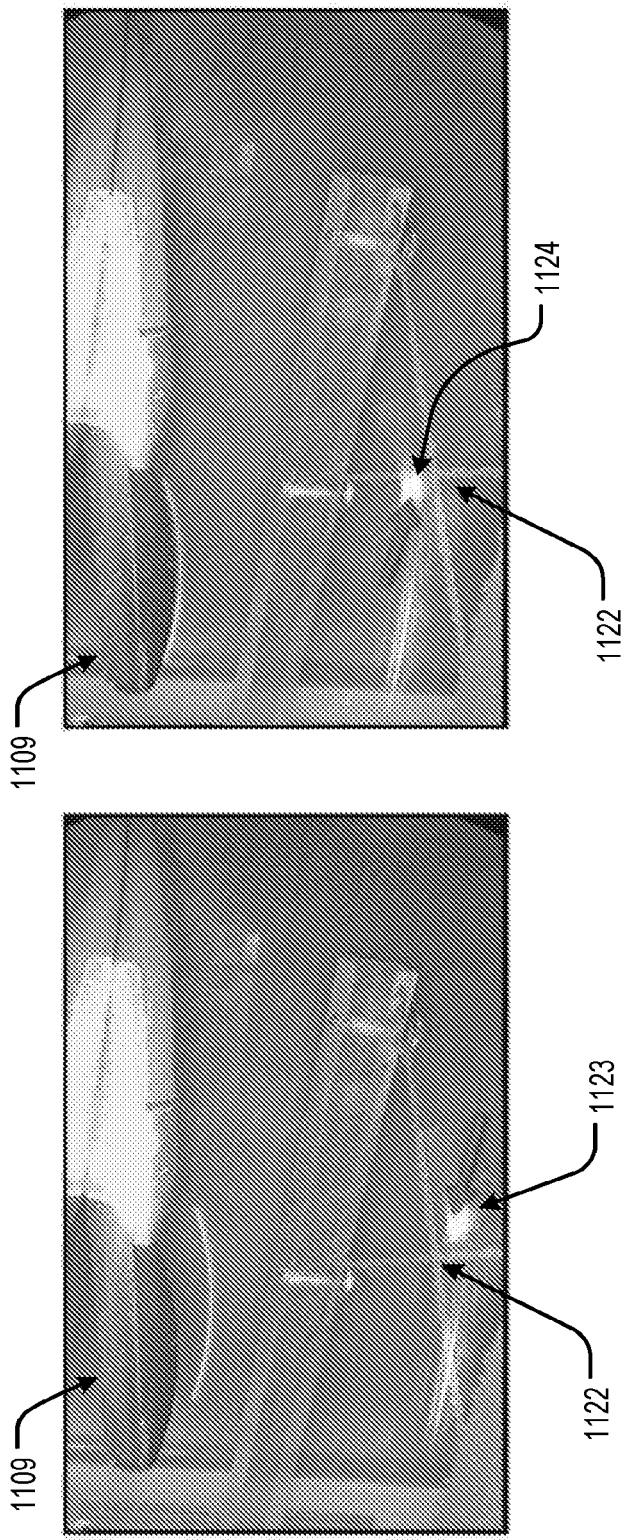
FIG. 11A is an illustration of an augmented reality visualization via hardware-based tracking approach, according to an exemplary embodiment of the present disclosure.
FIG. 11B is an illustration of an augmented reality visualization via hybrid tracking approach, according to an exemplary embodiment of the present disclosure.

In order to demonstrate improvement via hybrid tracking, and the above-described feature extraction approach, in particular, experiments were performed to measure and compare target registration error (TRE) between the EM tracking-based approach and the feature extraction approach described in FIG. 3. As illustrated in FIG. 11A and FIG. 11B, a target point 1122, the intersection of two cross wires immersed in a water tank, was imaged using an LUS transducer 1109. The target point 1122 along the imaging tip of the LUS transducer 1109 was viewed with a laparoscope, whose lens was similarly immersed in water. An LUS image from the LUS transducer 1109 was overlaid on the camera image through the EM tracking-based approach, shown in FIG. 11A, as well as via the feature extraction approach, shown in FIG. 11B. The estimated target point 1123, via the EM tracking-based approach, in the overlaid LUS image, and the refined target point 1124, via the feature extraction approach, in the overlaid LUS image, can then be identified and compared with the actual target point 1122 shown in the camera image. The Euclidean distance in the image plane, therefore, is the TRE.

Experiments with four different poses of the laparoscope and the LUS transducer were performed. The average TRE of the EM tracking-based approach was measured to be 102.0±60.5 pixel (8.2±4.9 mm) compared with 46.7±10.1 pixel (3.8±0.8 mm) for the feature extraction approach, with an image resolution of the camera of 1920×1280. As described, and illustrated in FIG. 11A and FIG. 11B, the feature extraction approach improved overlay accuracy of the original EM tracking-based approach. Moreover, the computer vision-based refinement process took on average 52 seconds, the major bottleneck being the C++ API interface required to read in a new candidate correction matrix. The total number of iteration steps in the optimization was fewer than 110 for each of the examples tried.

Figure 12A:
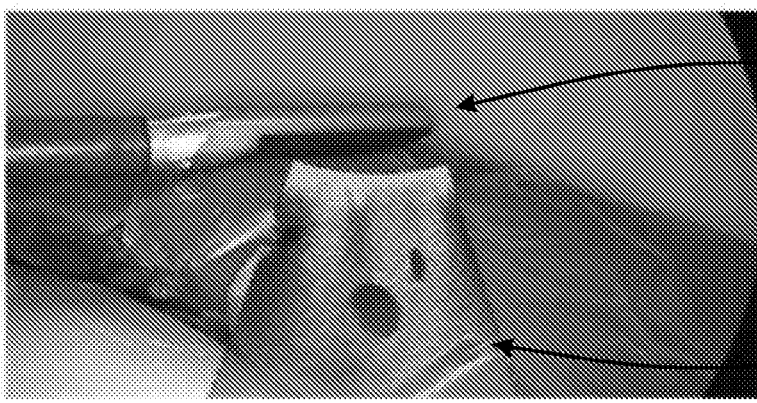
FIG. 12A is an illustration of an example of an augmented reality visualization via hardware-based tracking approach, according to an exemplary embodiment of the present disclosure.
Figure 12B:
FIG. 12B is an illustration of an example of an augmented reality visualization via hybrid tracking approach, according to an exemplary embodiment of the present disclosure.
Figure 12C:
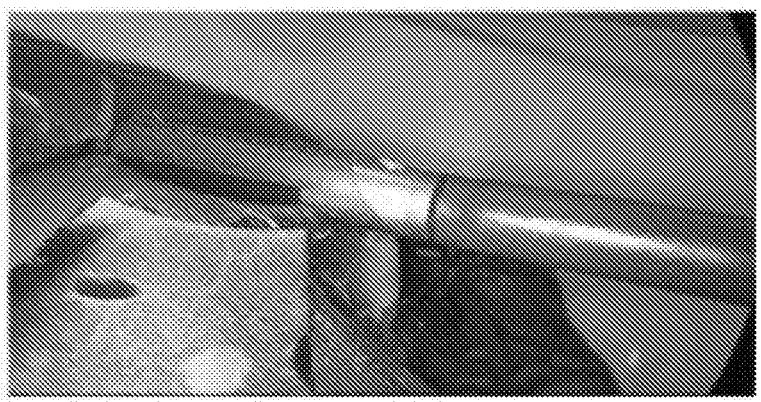
FIG. 12C is an illustration of an example of an augmented reality visualization via hardware-based tracking approach, according to an exemplary embodiment of the present disclosure.
Figure 12D:
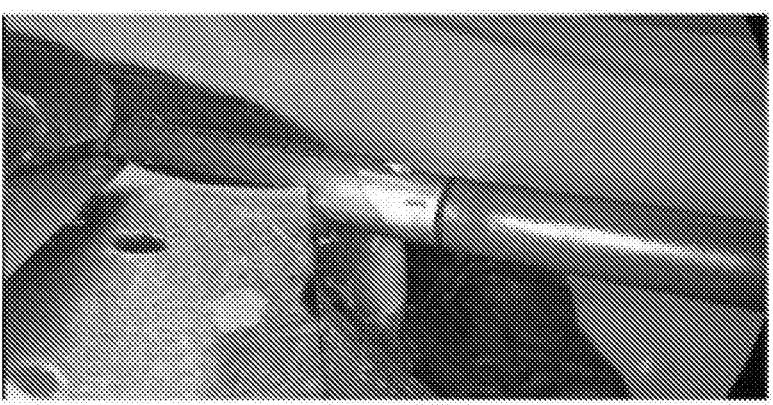
FIG. 12D is an illustration of an example of an augmented reality visualization via hybrid tracking approach, according to an exemplary embodiment of the present disclosure.

The feature extraction approach was further evaluated within a more clinically-relevant setting including testing images from phantoms via camera and ultrasound images. This evaluation, shown in FIG. 12A through FIG. 12D, wherein an ultrasound image 1217 is acquired via a LUS transducer 1209, illustrates the efficacy of the image processing and subsequent optimization performed by an image control device and as applied to a wire phantom. To this end, FIG. 12A and FIG. 12C represent hardware-based tracking estimations and FIG. 12B and FIG. 12D depict corresponding refinements of the hardware-based tracking estimations via the above-described feature extraction approach.

According to an embodiment, the present disclosure describes a computer vision-based refinement method for correction of registration error in hardware-based AR visualization. Initial hardware-based registration can provide an ROI for robust feature line detection, as well as a relatively close initialization for simplex-based optimization. A computer vision-based solution to refine image-to-video registration obtained using hardware-based tracking can also be implemented. A 3D LUS transducer model may be first projected on the camera image based on calibration results and tracking data. The model may then be registered with the actual LUS transducer using image processing and simplex optimization performed via image control device. Finally, the resulting correction matrix can be applied to the ultrasound image.

Embodiments of the present disclosure can also be implemented on a GPU, where the Hough Transform can be achieved in 3 ms, for instance, and the entire refinement process may require fewer than 1 second. In an embodiment, Stage 2A of the optimization approach may only use five of the six parameters associated with a rigid transformation. In another embodiment, the rotation about the LUS probe axis may be refined. Additionally or alternatively, determining how often the vision-based refinement should be repeated during AR visualization can also be identified and implemented.

According to an embodiment of the present disclosure, a processor can be embodied as various means for implementing the various functionalities of exemplary embodiments of the disclosed subject matter including, for example, a microprocessor, a coprocessor, a controller, a special-purpose integrated circuit such as, for example, an application specific integrated circuit (ASIC), a field programmable gate array (FPGA), a hardware accelerator, a processing circuitry, and the like. According to one or more embodiments of the present disclosure, the processor may be representative of a plurality of processors, or one or more multiple core processors, operating in concert. Further, the processor may be comprised of a plurality of transistors, logic gates, a clock, and, for example, an oscillator, other circuits or circuitry, and the like to facilitate performance of the functionality described herein. The processor may, but not need, include one or more accompanying digital signal processors. In some exemplary embodiments, the processor can be configured to execute instructions stored in a memory device or instructions otherwise accessible to the processor. The processor may be configured to operate such that the processor causes the apparatus, system, or method to perform various functionalities described herein.

Whether configured as hardware or via instructions stored on a computer-readable storage medium, or by a combination thereof, the processor may be an entity configured to perform, and/or cause a system or apparatus, according to embodiments of the present disclosure, to perform, operations according to embodiments of the present disclosure while configured accordingly, including some or all of the operations associated with FIG. 3 and/or FIG. 5 discussed above. Thus, in exemplary embodiments where the processor is embodied as, or is part of, an ASIC, FPGA, or the like, the processor can be specifically configured hardware for conducting, or causing the performance of, the operations described herein. Alternatively, in exemplary embodiments, where the processor is embodied as an executor of instructions stored on a computer-readable storage medium, the instructions can specifically configure the processor to perform, and/or cause the performance of, the methods and operations described herein. In some exemplary embodiments, the processor can be a processor of a specific device configured for employing exemplary embodiments of the present disclosure by further configuration of the processor via executed instructions for performing, and/or causing the performance of, the algorithms, methods, and operations described herein.

According to embodiments of the present disclosure, a memory device may be one or more computer-readable storage media that may include volatile and/or non-volatile memory. In some exemplary embodiments, the memory device can include Random Access Memory (RAM) including dynamic and/or static RAM, on-chip or off-chip cache memory, and the like. Further, the memory device may include non-volatile memory, which may be embedded and/or removable, and may include, for example, read-only memory, flash memory, magnetic storage devices including hard disks, magnetic tape, and the like, optical disc drives and/or media, non-volatile random access memory (NVRAM), and the like. The memory device may include a cache area for temporary storage of data. In this regard, at least a portion or the entire memory device may be included within the processor.

Further, the memory device may be configured to store information, data, applications, computer-readable program code instructions, and the like for enabling the processor and the exemplary apparatus or system to carry out various functions in accordance with exemplary embodiments of the present disclosure described herein. For example, the memory device may be configured to buffer input data for processing by the processor. Additionally, or alternatively, the memory device may be configured to store instructions for execution by the processor.

Figure 13:
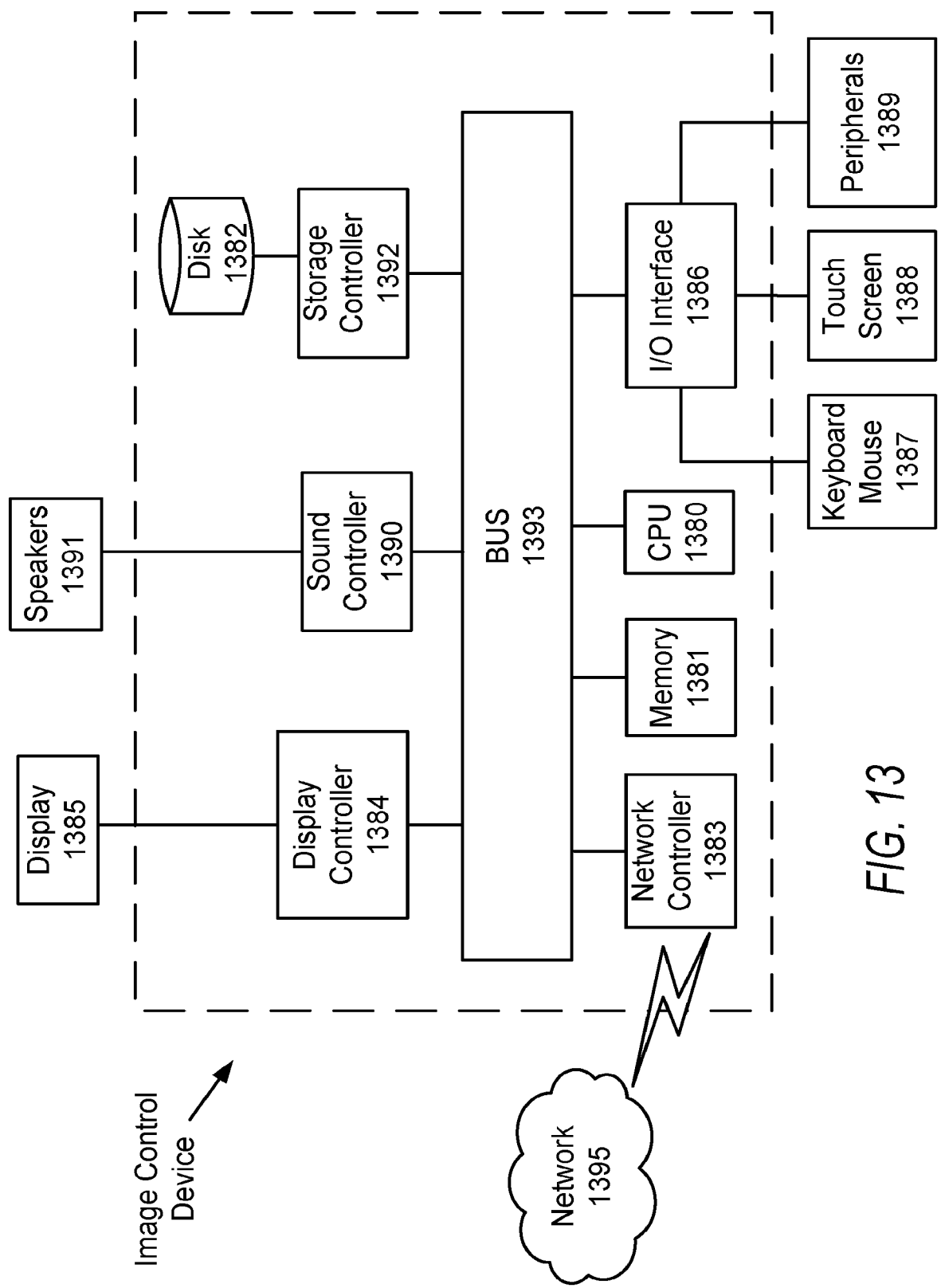
FIG. 13 is a description of a hardware device implementing a hybrid based approach, according to an exemplary embodiment of the present disclosure.

In another embodiment, the processor can be embodied within an image control device, the image control device being configured to execute the operations associated with, at least, FIG. 3 and FIG. 5, described above. To this end, a hardware description of an image control device according to exemplary embodiments of the present disclosure is described with reference to FIG. 13. In FIG. 13, the image control device includes a CPU 1380 which performs the processes described above. The process data and instructions may be stored in memory 1381. These processes and instructions may also be stored on a storage medium disk 1382 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the image control device communicates, such as a server or computer.

Further, the claimed advancements may be provided as a utility application, background daemon, or component of an operating system, or combination thereof, executing in conjunction with CPU 1380 and an operating system such as Microsoft Windows 7, UNIX, Solaris, LINUX, Apple MAC-OS and other systems known to those skilled in the art.

The hardware elements in order to achieve the image control device may be realized by various circuitry elements, known to those skilled in the art. For example, CPU 1380 may be a Xenon or Core processor from Intel of America or an Opteron processor from AMD of America, or may be other processor types that would be recognized by one of ordinary skill in the art. Alternatively, the CPU 1380 may be implemented on an FPGA, ASIC, PLD or using discrete logic circuits, as one of ordinary skill in the art would recognize. Further, CPU 1380 may be implemented as multiple processors cooperatively working in parallel to perform the instructions of the inventive processes described above.

The image control device in FIG. 13 also includes a network controller 1383, such as an Intel Ethernet PRO network interface card from Intel Corporation of America, for interfacing with network 1395. As can be appreciated, the network 1395 can be a public network, such as the Internet, or a private network such as an LAN or WAN network, or any combination thereof and can also include PSTN or ISDN sub-networks. The network 1395 can also be wired, such as an Ethernet network, or can be wireless such as a cellular network including EDGE, 3G and 4G wireless cellular systems. The wireless network can also be WiFi, Bluetooth, or any other wireless form of communication that is known.

The image control device further includes a display controller 1384, such as a NVIDIA GeForce GTX or Quadro graphics adaptor from NVIDIA Corporation of America for interfacing with display 1385, such as a Hewlett Packard HPL2445w LCD monitor. A general purpose I/O interface 1386 interfaces with a keyboard and/or mouse 1387 as well as a touch screen panel 1388 on or separate from display 1385. General purpose I/O interface also connects to a variety of peripherals 1389 including printers and scanners, such as an OfficeJet or DeskJet from Hewlett Packard.

A sound controller 1390 is also provided in the image control device, such as Sound Blaster X-Fi Titanium from Creative, to interface with speakers/microphone 1391 thereby providing sounds and/or music.

The general purpose storage controller 1392 connects the storage medium disk 1382 with communication bus 1393, which may be an ISA, EISA, VESA, PCI, or similar, for interconnecting all of the components of the image control device. A description of the general features and functionality of the display 1385, keyboard and/or mouse 1387, as well as the display controller 1384, storage controller 1392, network controller 1383, sound controller 1390, and general purpose I/O interface 1386 is omitted herein for brevity as these features are known.

Embodiments of the present disclosure may also be as set forth in the following parenthetical s.

(1) A tracking system for augmented reality, the tracking system comprising an imaging modality configured to obtain a medical image, a display configured to display the medical image, and an image control device including a processing circuitry configured to acquire spatial data of a real object, observed in the medical image of the imaging modality, via a first tracking method, determine a projection matrix based upon the acquired spatial data of the real object, project a virtual object onto the medical image of the imaging modality, the virtual object being a projection of the real object according to the projection matrix, calculate a correction matrix, update the projection of the virtual object according to the correction matrix, and modify the display of the medical image based on the updated projection.

(2) The tracking system according to (1), wherein the projection of the virtual object is fused with a time-matched medical image of the imaging modality.

(3) The tracking system according to either (1) or (2), wherein the first tracking method is an electromagnetic-based tracking system.

(4) The tracking system according to any of (1) to (3), wherein calculation of the correction matrix includes optimization of at least one cost function.

(5) The tracking system according to any of (1) to (4), wherein the at least one cost function is based upon a comparison of a position of one or more features of the virtual object and a position of a corresponding one or more features of the real object.

(6) The tracking system according to any of (1) to (5), wherein the position of the one or more features of the virtual object and the position of the corresponding one or more features of the real object is determined according to a second tracking method.

(7) The tracking system according to any of (1) to (6), wherein calculation of the correction matrix includes determining a spatial relationship between one or more features of the virtual object and a corresponding one or more features of the real object, the one or more features of the virtual object and the corresponding one or more features of the real object including a user-defined pattern.

(8) The tracking system according to any of (1) to (7), wherein calculation of the correction matrix includes determining a spatial relationship between one or more features of the virtual object and a corresponding one or more features of the real object, wherein the one or more features of the virtual object and the corresponding one or more features of the real object are determined based upon a classifier, the classifier being trained to detect the real object.

(9) A method for augmented reality, comprising acquiring, via processing circuitry, spatial data of a real object observed in a medical image of an imaging modality via a first tracking method, determining, via the processing circuitry, a projection matrix based upon the acquired spatial data of the real object, projecting, via the processing circuitry, a virtual object onto the medical image of the imaging modality, the virtual object being a projection of the real object according to the projection matrix, calculating, via the processing circuitry, a correction matrix, updating, via the processing circuitry, the projection of the virtual object according to the correction matrix, and displaying, via the processing circuitry, the medical image, wherein the displayed medical image is modified based upon the updated projection.

(10) The method according to (9), wherein calculating the correction matrix includes optimization of at least one cost function.

(11) The method according to either (9) or (10), wherein the at least one cost function is based upon a comparison of a position of one or more features of the virtual object and a position of a corresponding one or more features of the real object.

(12) The method according to any of (9) to (11), wherein the position of the one or more features of the virtual object and the position of the corresponding one or more features of the real object is determined according to a second tracking method.

(13) The method according to any of (9) to (12), wherein calculating the correction matrix includes determining a spatial relationship between one or more features of the virtual object and a corresponding one or more features of the real object, the one or more features of the virtual object and the corresponding one or more features of the real object including a user-defined pattern.

(14) The method according to any of (9) to (13), wherein calculating the correction matrix includes determining a spatial relationship between one or more features of the virtual object and a corresponding one or more features of the real object, wherein the one or more features of the virtual object and the corresponding one or more features of the real object are determined based upon a classifier, the classifier being trained to detect the real object.

(15) A non-transitory computer-readable storage medium storing computer-readable instructions that, when executed by a computer, cause the computer to perform a method of augmented reality, comprising acquiring spatial data of a real object observed in a medical image of an imaging modality via a first tracking method, determining a projection matrix based upon the acquired spatial data of the real object, projecting a virtual object onto the medical image of the imaging modality, the virtual object being a projection of the real object according to the projection matrix, calculating a correction matrix, updating the projection of the virtual object according to the correction matrix, and displaying the medical image, wherein the displayed medical image is modified based upon the updated projection.

(16) The method according to (15), wherein calculating the correction matrix includes optimization of at least one cost function.

(17) The method according to either (15) or (16), wherein the at least one cost function is based upon a comparison of a position of one or more features of the virtual object and a position of a corresponding one or more features of the real object.

(18) The method according to any of (15) to (17), wherein the position of the one or more features of the virtual object and the position of the corresponding one or more features of the real object is determined according to a second tracking method.

(19) The method according to any of (15) to (18), wherein calculating the correction matrix includes determining a spatial relationship between one or more features of the virtual object and a corresponding one or more features of the real object, the one or more features of the virtual object and the corresponding one or more features of the real object including a user-defined pattern.

(20) The method according to any of (15) to (19), wherein calculating the correction matrix includes determining a spatial relationship between one or more features of the virtual object and a corresponding one or more features of the real object, wherein the one or more features of the virtual object and the corresponding one or more features of the real object are determined based upon a classifier, the classifier being trained to detect the real object.

Obviously, numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A tracking system for augmented reality, the tracking system comprising:
   an imaging modality configured to obtain a medical image;
   a display configured to display the medical image; and
   an image control device including processing circuitry configured to
   acquire spatial data of a real object, the real object being a medical surgical tool observed in the medical image of the imaging modality, via a first tracking method,
   determine a projection matrix based upon the acquired spatial data of the real object, the acquired spatial data corresponding to points observed on the real object,
   project a virtual object onto the medical image of the imaging modality, the virtual object being a projection of a shape model of the real object according to the projection matrix,
   calculate a correction matrix based on the projection of the virtual object,
   update the projection of the virtual object according to the correction matrix, and
   modify the display of the medical image based on the updated projection, the medical image including an ultrasound image overlayed on a camera image.

2. The tracking system according to claim 1, wherein the projection of the virtual object is fused with a time-matched medical image of the imaging modality.

3. The tracking system according to claim 1, wherein the first tracking method is an electromagnetic-based tracking system.

4. The tracking system according to claim 1, wherein calculation of the correction matrix includes optimization of at least one cost function.

5. The tracking system according to claim 4, wherein the at least one cost function is based upon a comparison of a position of one or more features of the virtual object and a position of a corresponding one or more features of the real object.

6. The tracking system according to claim 5, wherein the position of the one or more features of the virtual object and the position of the corresponding one or more features of the real object is determined according to a second tracking method.

7. The tracking system according to claim 1, wherein calculation of the correction matrix includes determining a spatial relationship between one or more features of the virtual object and a corresponding one or more features of the real object, the one or more features of the virtual object and the corresponding one or more features of the real object including a user-defined pattern.

8. The tracking system according to claim 1, wherein calculation of the correction matrix includes determining a spatial relationship between one or more features of the virtual object and a corresponding one or more features of the real object, wherein the one or more features of the virtual object and the corresponding one or more features of the real object are determined based upon a classifier, the classifier being trained to detect the real object.

9. A method for augmented reality, comprising:
   acquiring, via processing circuitry, spatial data of a real object, the real object being a medical surgical tool observed in a medical image of an imaging modality via a first tracking method;
   determining, via the processing circuitry, a projection matrix based upon the acquired spatial data of the real object, the acquired spatial data corresponding to points observed on the real object;
   projecting, via the processing circuitry, a virtual object onto the medical image of the imaging modality, the virtual object being a projection of a shape model of the real object according to the projection matrix;
   calculating, via the processing circuitry, a correction matrix based on the projection of the virtual object;
   updating, via the processing circuitry, the projection of the virtual object according to the correction matrix; and
   displaying, via the processing circuitry, the medical image, wherein the displayed medical image includes an ultrasound image overlayed on a camera image and wherein the displayed medical image is modified based upon the updated projection.

10. The method according to claim 9, wherein calculating the correction matrix includes optimization of at least one cost function.

11. The method according to claim 10, wherein the at least one cost function is based upon a comparison of a position of one or more features of the virtual object and a position of a corresponding one or more features of the real object.

12. The method according to claim 11, wherein the position of the one or more features of the virtual object and the position of the corresponding one or more features of the real object is determined according to a second tracking method.

13. The method according to claim 9, wherein calculating the correction matrix includes determining a spatial relationship between one or more features of the virtual object and a corresponding one or more features of the real object, the one or more features of the virtual object and the corresponding one or more features of the real object including a user-defined pattern.

14. The method according to claim 9, wherein calculating the correction matrix includes determining a spatial relationship between one or more features of the virtual object and a corresponding one or more features of the real object, wherein the one or more features of the virtual object and the corresponding one or more features of the real object are determined based upon a classifier, the classifier being trained to detect the real object.

15. A non-transitory computer-readable storage medium storing computer-readable instructions that, when executed by a computer, cause the computer to perform a method of augmented reality, comprising:
   acquiring spatial data of a real object, the real object being a medical surgical tool observed in a medical image of an imaging modality, via a first tracking method;
   determining a projection matrix based upon the acquired spatial data of the real object the acquired spatial data corresponding to points observed on the real object;
   projecting a virtual object onto the medical image of the imaging modality, the virtual object being a projection of a shape model of the real object according to the projection matrix;
   calculating a correction matrix based on the projection of the virtual object;
   updating the projection of the virtual object according to the correction matrix; and
   displaying the medical image, wherein the displayed medical image is modified based upon the updated projection and wherein the medical image includes an ultrasound image overlayed on a camera image.

16. The non-transitory computer-readable storage medium according to claim 15, wherein calculating the correction matrix includes optimization of at least one cost function.

17. The non-transitory computer-readable storage medium according to claim 16, wherein the at least one cost function is based upon a comparison of a position of one or more features of the virtual object and a position of a corresponding one or more features of the real object.

18. The non-transitory computer-readable storage medium according to claim 17, wherein the position of the one or more features of the virtual object and the position of the corresponding one or more features of the real object is determined according to a second tracking method.

19. The non-transitory computer-readable storage medium according to claim 15, wherein calculating the correction matrix includes determining a spatial relationship between one or more features of the virtual object and a corresponding one or more features of the real object, the one or more features of the virtual object and the corresponding one or more features of the real object including a user-defined pattern.

20. The non-transitory computer-readable storage medium according to claim 15, wherein calculating the correction matrix includes determining a spatial relationship between one or more features of the virtual object and a corresponding one or more features of the real object, wherein the one or more features of the virtual object and the corresponding one or more features of the real object are determined based upon a classifier, the classifier being trained to detect the real object.

* * * * *